Figure 1:
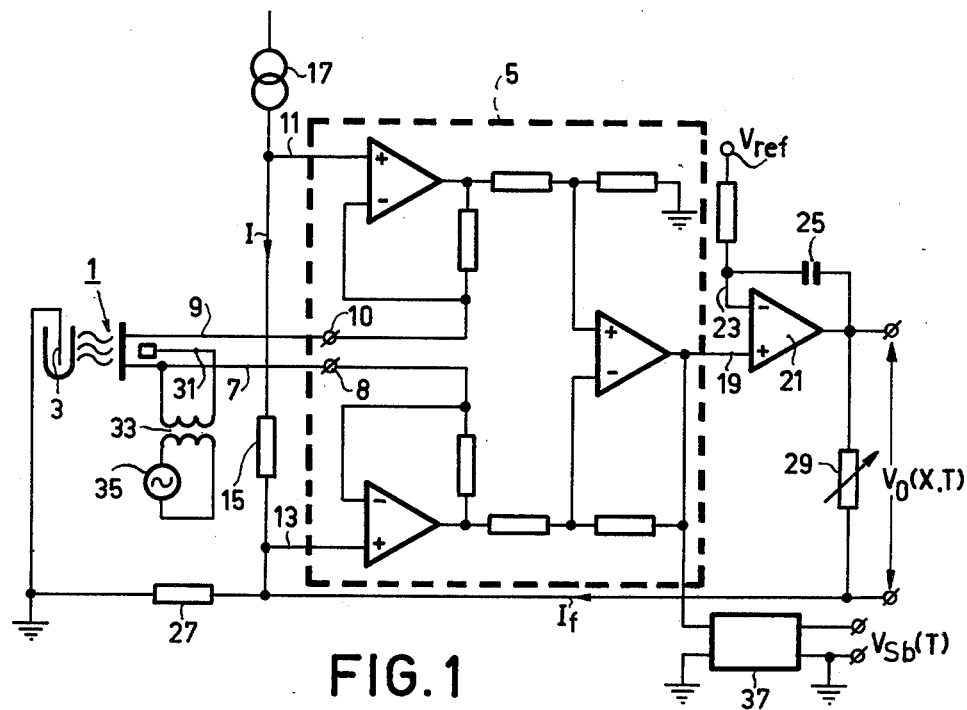

United States Patent [19]

Bergveld

[11] 4,267,504
[45] May 12, 1981

[54] DEVICE FOR MEASURING A QUANTITY WHICH INFLUENCES A FIELD-EFFECT TRANSISTOR

[75] Inventor: Piet Bergveld, Enschede, Netherlands

[73] Assignee: U.S. Philips Corporation, New York, N.Y.

[21] Appl. No.: 86,922

[22] Filed: Oct. 22, 1979

[30] Foreign Application Priority Data

Nov. 6, 1978 [NL] Netherlands .................. 7811001

[51] Int. Cl.³ ............................................ G01R 27/02
[52] U.S. Cl. ..................................... 324/62; 324/425; 324/459
[58] Field of Search ............... 324/62, 459, 464, 425, 324/431

[56] References Cited

U.S. PATENT DOCUMENTS 3,328,685  6/1967  Hewlett .................................. 324/62
3,490,039  1/1970  Tsao ...................................... 324/62

OTHER PUBLICATIONS

Stetzler, Apparatus for Measuring Small Value Resistance, Western Electric Technical Digest, No. 44, Oct. 1976, pp. 51 and 52.

Primary Examiner—Stanley T. Krawczewicz
Attorney, Agent, or Firm—William J. Streeter; Bernard Franzblau

[57] ABSTRACT

A device for measuring a quantity which influences a field-effect transistor which is included in a measuring circuit as a variable resistance. To compensate for temperature-dependent changes of the field-effect transistor, an auxiliary signal, having a frequency located outside the frequency range of the quantity to be measured, is applied to the transistor. The two signals are separated from one another again after having been processed by the measuring circuit.

3 Claims, 2 Drawing Figures

DEVICE FOR MEASURING A QUANTITY WHICH INFLUENCES A FIELD-EFFECT TRANSISTOR

The invention relates to a device for measuring a quantity which influences a field-effect transistor having a source electrode and a drain electrode, connected to terminals of a measuring circuit so that changes in the resistance between these electrodes influence the output voltage of the measuring circuit.

An example of such a device is described in the periodical "IEEE Transactions on Biomedical Engineering" Vol. BME-19, No. 5, September 1972, pages 342–351. In this example the field-effect transistor is an ion-sensitive field-effect transistor and the quantity to be measured is the concentration of certain ions in a solution.

Field-effect transistors have the drawback that they are not only sensitive to the quantity to be measured but also to the ambient temperature. It is, in principle, indeed possible to arrange a second temperature-sensitive element near the field-effect transistor in order to obtain a separate indication of the temperature, but then it can never be known with certainty whether the two elements are always at exactly the same temperature and whether they react in exactly the same manner to temperature changes. A very accurate and reliable temperature compensation is therefore not possible.

It is an object of the invention to provide a device of the type mentioned in the preamble wherein a temperature compensation is possible with a considerably greater reliability and accuracy than with the known device.

The device according to the invention is therefore characterized in that an auxiliary signal is applied to the field-effect transistor, the frequency of which is outside the frequency range in which changes in the quantity to be measured occur, and in that the measuring circuit comprises means for separating signals at the frequency of the auxiliary signal from signals located within said frequency range.

According to the invention a preferred embodiment of the device is characterized in that the quantity to be measured is applied to the field-effect transistor via a first input and the auxiliary signal via a second input.

Figure 2:
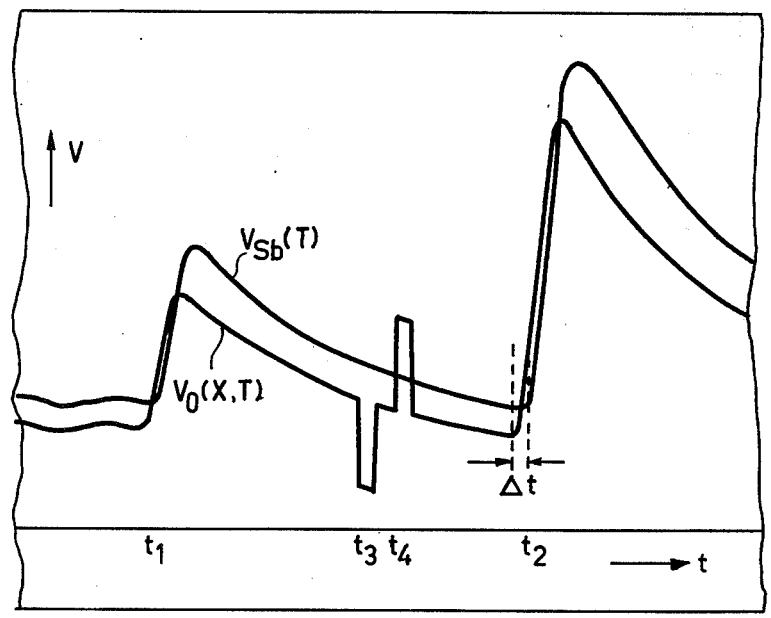

The invention will now be further explained with reference to the drawing, in which:

FIG. 1 is a circuit diagram of an embodiment of a device according to the invention and FIG. 2 shows measuring curves obtained by means of such a device.

The device shown in FIG. 1 comprises a field-effect transistor 1 for measuring ion activity in a solution, such as, for example, described in the above-cited articles in "IEEE Transactions on Biomedical Engineering" or in Netherlands patent application No. 7602619, which was laid open to public inspection. In addition, there is a grounded reference electrode 3 in the solution.

In addition, the device comprises an instrumentation amplifier 5 which is known per se (see "Archiv für technische Messen," page Z 6343-6, April 1973) and which therefore needs no further explanation. By means of the conductors 7 and 9, connected to its source electrode and its drain electrode, respectively, the field effect transistor 1 is included as a variable resistance in the circuit of the instrumentation amplifier 5, namely between the terminals 8 and 10, respectively, thereof, so that the resistance between the source electrode and the drain electrode influences the gain of the instrumentation amplifier. The input voltage of the instrumentation amplifiers, applied via conductors 11 and 13, is constituted by the voltage across a resistor 15, which is fed with a constant current I from a current source 17. Consequently, this voltage is constant so that the voltage at the output 19 only depends on the resistance in the field effect transistor 1. This output voltage is applied to a differential amplifier 21 and is compared with an adjustable reference voltage $V_{ref}$ which is also applied to this differential amplifier via a conductor 23. A feedback capacitor 25 determines the cut-off frequency of the differential amplifier 21.

The output current $I_f$ of the differential amplifier 21 flows through a voltage divider which is formed by a fixed resistor 27 and a variable resistor 29, which effects in known manner a negative feedback of the circuit formed by field-effect transistor 1 and the amplifiers 5 and 21. An output voltage $V_o$ which depends on the quantity X to be measured, i.e. the ion activity, on the temperature T of the field-effect transistor 1, on the reference voltage $V_{ref}$ and on the ratio between the resistors 27 and 29 is then measured across the resistor 29. By choosing a predetermined value for the reference voltage $V_{ref}$ a zero point adjustment for the measurement can be effected, whereas the sensitivity can be determined by means of the resistor 29.

To determine the influence of the temperature T, the substrate of the field-effect transistor 1 is connected by means of an electrode terminal 31 and via a transformer 33 to a voltage source 35 which applies an auxiliary signal to the field-effect transistor. The frequency of this signal is outside the frequency range in which changes in the quantity X to be measured occur. The capacitor 25 is, for example, chosen so that the differential amplifier 21 handles signals up to 3 kHz, while the frequency of the auxiliary signal is 30 kHz.

The auxiliary signal and also the quantity to be measured influence the resistance of the field-effect transistor 1. So the signal at the output 19 of the instrumentation amplifier 5 is composed of a low-frequency component, which depends on the quantity X to be measured and a high-frequency component, which depends on the auxiliary signal. Furthermore, both components depend in the same manner on the temperature T of the field-effect transistor. The output 19 is not only connected to the differential amplifier 21 but also to the input of a detector 37, which is known per se and is arranged to measure the amplitude of signals at the frequency of the auxiliary signal. Consequently, at the output of this detector there appears a voltage $V_{Sb}$ which, besides its dependency on the constant value of the auxiliary signal, depends exclusively on the temperature T of the field-effect transistor 1. So, when this temperature changes, the voltages $V_o$ and $V_{Sb}$ will change in an identical manner.

To illustrate the operation described above, FIG. 2 shows the variation in the two voltages as a function of the time, the curve for $V_{Sb}$ being shown with a small delay $\Delta t$ to prevent, for clarity's sake, the two curves from partially coinciding. The arrangement to which this relates is an arrangement wherein the field-effect transistor is a so-called MOS transistor having a gate electrode to which a voltage which constitutes the input quantity X can be applied. At the instants $t_1$ and $t_2$ the transistor was heated for a short period of time, in response to which the two voltages $V_o$ and $V_{Sb}$ increased in the same manner. At the instants $t_3$ and $t_4$ a negative and a positive voltage, respectively, were applied to the gate electrode, causing the voltage $V_o$ to change, whereas the voltage $V_{Sb}$ did not react.

It will be apparent that when the voltage $V_{Sb}$ is amplified (attenuated) by a suitable factor A and the voltages are thereafter subtracted from one another, the resulting voltage $V_o(X, T)-A \cdot V_{Sb}(T)$ depends exclusively on the quantity X to be measured and no longer on the temperature. This operation can be performed by means of a differential amplifier (not shown) which is known per se. If so desired, the voltage $V_{Sb}$ can alternatively be used for, for example, controlling the reference voltage $V_{ref}$ or for controlling an amplifier (not shown) with which $V_o$ is still further amplified.

The device shown in FIG. 1 is only given by way of example and can be altered in many respects. Any other suitable measuring circuit can be used instead of the instrumentation amplifier 5 and differential amplifier 21 shown in the drawing. Examples of such circuits can be found in the above-mentioned article in the "IEEE Transactions on Biomedical Engineering".

Applying the auxiliary signal can be done in a manner different from the manner shown, for example by irradiating the field-effect transistor with modulated light or by applying the signal via a gate electrode when a MOS-transistor is used.

What is claimed is:

1. A device for measuring a quantity comprising, a field-effect transistor having a source and a drain electrode, said field-effect transistor being located so as to be influenced by said quantity to be measured, means connecting said electrodes to terminals of a measuring circuit so that changes in the resistance between said electrodes influence the output voltage of the measuring circuit, means for applying to the field-effect transistor an auxiliary signal the frequency of which is located outside the frequency range in which changes of the quantity to be measured occur, and wherein the measuring circuit comprises means for separating signals at the frequency of the auxiliary signal from signals within the said frequency range.

2. A device as claimed in claim 1, characterized in that the quantity to be measured is applied to the field-effect transistor (1) via a first input and the auxiliary signal via a second input.

3. A device as claimed in claim 2, characterized in that the second input of the field-effect transistor comprises an electric connection which is connected to a substrate of said transistor.

* * * * *

UNITED STATES PATENT OFFICE
CERTIFICATE OF CORRECTION

Patent No. 4,267,504        Dated 5/12/81

Inventor(s) Piet Bergveld

It is certified that error appears in the above-identified patent and that said Letters Patent are hereby corrected as shown below:

Col. 4, Line 20, After "transistor" delete "(1)"

Signed and Sealed this

Twenty-second Day of September 1981

[SEAL]

Attest:

GERALD J. MOSSINGHOFF

Attesting Officer    Commissioner of Patents and Trademarks